(12) United States Patent
Watson et al.

(10) Patent No.: US 8,465,704 B2
(45) Date of Patent: Jun. 18, 2013

(54) METHOD AND APPARATUS FOR DISINFECTING AND/OR DEODORIZING AN ARTICLE

(75) Inventors: Eric K. Watson, Crestwood, KY (US); John K. Besore, Prospect, KY (US); Subhash Viswanathan Kollengode, Andhra Pradesh (IN); Christopher Durand, Toledo, OH (US); Brian Michael Schork, Louisville, KY (US); Sarah Lynn Kirchoff, Hartland, WI (US)

(73) Assignee: General Electric Company, Schenectady, NY (US)

( * ) Notice: Subject to any disclaimer, the term of this patent is extended or adjusted under 35 U.S.C. 154(b) by 559 days.

(21) Appl. No.: 12/621,947

(22) Filed: Nov. 19, 2009

(65) Prior Publication Data

US 2011/0002810 A1    Jan. 6, 2011

Related U.S. Application Data

(60) Provisional application No. 61/222,796, filed on Jul. 2, 2009.

(51) Int. Cl.
*B01J 19/12* (2006.01)
*A61L 9/00* (2006.01)
*F01N 3/20* (2006.01)

(52) U.S. Cl.
USPC ............... 422/186.12; 422/5; 422/105

(58) Field of Classification Search
USPC ........................ 422/5, 186.12, 105
See application file for complete search history.

(56) References Cited

U.S. PATENT DOCUMENTS

| 5,666,743 | A | 9/1997 | Dawson |
| 5,681,370 | A | 10/1997 | McMahon |
| 7,658,891 | B1 * | 2/2010 | Barnes ................. 422/186.03 |
| 2003/0097762 | A1 | 5/2003 | Hsu |
| 2005/0120757 | A1 | 6/2005 | Jackson |
| 2005/0129571 | A1 * | 6/2005 | Centanni ................. 422/31 |
| 2005/0283282 | A1 | 12/2005 | Pervaiz |
| 2008/0031770 | A1 | 2/2008 | Heselton et al. |
| 2008/0159907 | A1 | 7/2008 | Joshi et al. |

FOREIGN PATENT DOCUMENTS

| EP | 0 841 427 A1 | 5/1998 |
| JP | 4156853 A | 5/1992 |
| JP | 11206316 A * | 8/1999 |
| JP | 2003-200029 | 7/2003 |
| WO | WO 2006/096990 A1 | 9/2006 |
| WO | WO 2006/131148 A1 | 12/2006 |

* cited by examiner

*Primary Examiner* — Kevin Joyner
(74) *Attorney, Agent, or Firm* — Fay Sharpe LLP

(57) ABSTRACT

An apparatus for disinfecting and/or deodorizing an article comprises a cabinet defining a compartment configured to receive the article. A regenerative dryer is positioned with respect to the compartment and is configured to dehydrate air flowing into an ozone generator. The ozone generator is in communication with the dryer and is positioned with respect to the compartment. The ozone generator is configured to selectively generate ozone. The generated ozone is introduced into the compartment. An ozone conversion device is positioned with respect to the compartment and is configured to selectively convert ozone back to oxygen. A controller is configured to selectively activate the dryer, ozone generator and ozone conversion device.

18 Claims, 16 Drawing Sheets

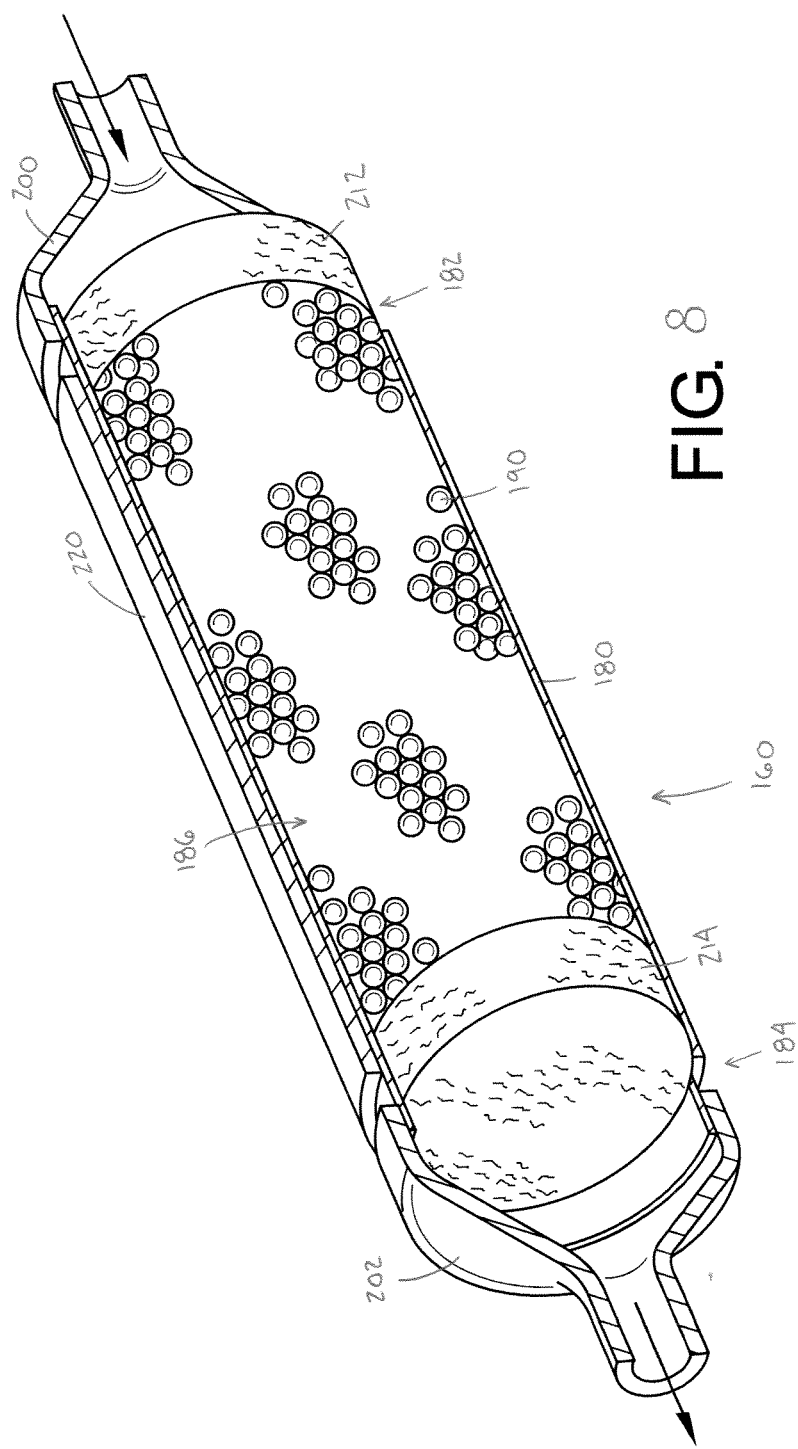

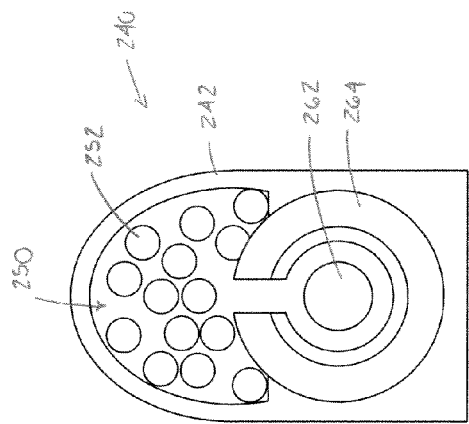
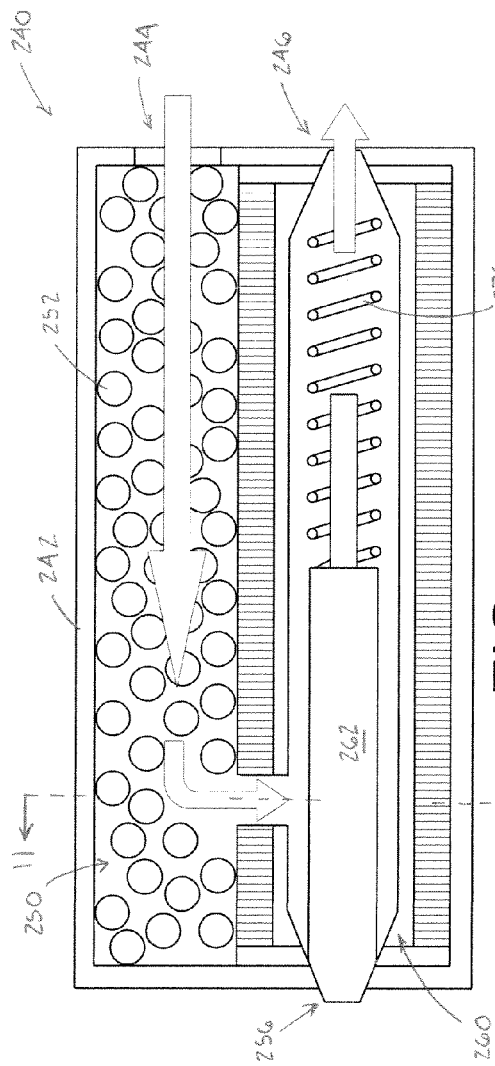
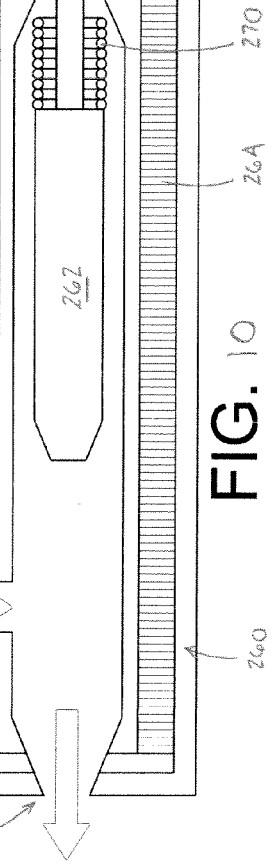

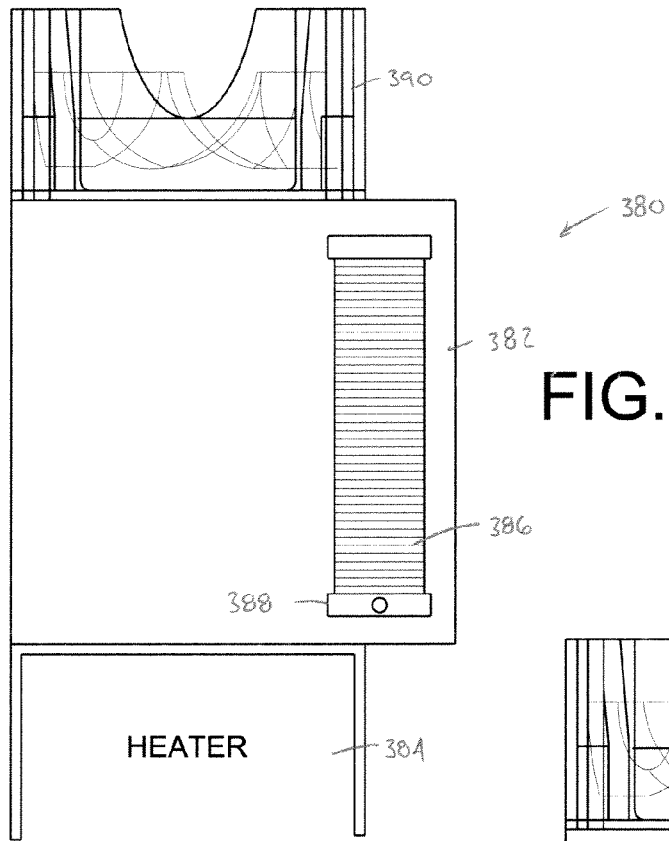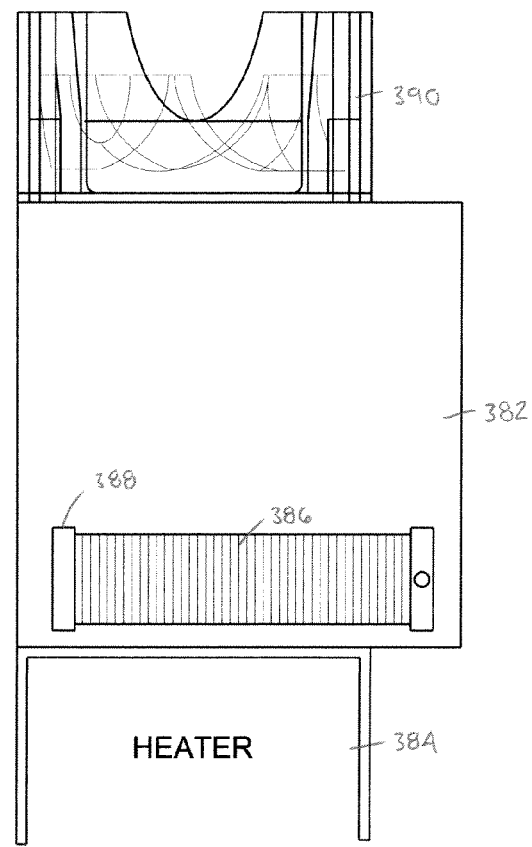

METHOD AND APPARATUS FOR
DISINFECTING AND/OR DEODORIZING AN
ARTICLE

This application claims the priority benefit of co-pending provisional application Ser. No. 61/222,796, filed 2 Jul. 2009.

BACKGROUND OF THE DISCLOSURE

The present disclosure relates generally to appliances and, more particularly, to apparatus for disinfecting and/or deodorizing an article.

Conventional home appliances, such as washing machines and/or drying machines disinfect and/or deodorize articles, such as clothes, by washing and drying the articles. However, such washing and drying processes take a considerable amount of time, and may only partially remove undesirable odors and/or microorganisms. For example, some odors, such as cigarette and shoe odors may not be effectively removed by the washing and drying processes. In addition, some articles, such as leather shoes and jackets, may not be washable and/or dryable to remove the undesirable odors and/or the microorganisms therefrom.

SUMMARY OF THE DISCLOSURE

In accordance with one aspect, an apparatus for disinfecting and/or deodorizing an article comprises a cabinet defining a compartment configured to receive the article. A regenerative dryer is positioned with respect to the compartment and is configured to dehydrate air flowing into an ozone generator. The dryer includes a housing having an air inlet and an air outlet located downstream from the air inlet. The housing defines a chamber. A dehydrating agent is disposed within the chamber for absorbing moisture laden in the air. The dehydrating agent is operatively regenerated by heat for vaporizing and removing moisture in the dehydrating agent when saturated with the moisture. The ozone generator is in communication with the dryer and is positioned with respect to the compartment. The ozone generator is configured to selectively generate ozone. The generated ozone is introduced into the compartment. An ozone conversion device is positioned with respect to the compartment and is configured to selectively convert ozone back to oxygen. A controller is configured to selectively activate the dryer, ozone generator and ozone conversion device.

In accordance with another aspect, an apparatus for disinfecting and/or deodorizing an article comprises a cabinet defining a compartment configured to receive the article. A regenerative dryer is positioned with respect to the compartment and is configured to dehydrate air flowing into an ozone generator. The dryer includes a housing having an air inlet and an air outlet located downstream from the air inlet. The housing defines a chamber. A dehydrating agent is disposed within the chamber for absorbing moisture laden in the air. The dehydrating agent is operatively regenerated by heat for vaporizing and removing moisture in the dehydrating agent when saturated with the moisture. The ozone generator is in communication with the dryer and is positioned with respect to the compartment. The ozone generator is configured to selectively generate ozone. The generated ozone is introduced into the compartment. An ozone conversion device is positioned with respect to the compartment and is configured to selectively convert ozone back to oxygen. The ozone conversion device includes a fan and a housing for housing at least one of a heater and a catalyst. In a first airflow mode, the heater is de-energized and the fan circulates generated ozone through the compartment, the ozone airflow bypassing the catalyst. In a second airflow mode, the heater is energized and the fan directs the heated ozone airflow to the catalyst for converting ozone to oxygen. A controller is configured to selectively activate the dryer, ozone generator and ozone conversion device.

In accordance with yet another aspect, a method for disinfecting and/or deodorizing an article comprising providing an appliance including a cabinet which defines a compartment. An article is placed within the compartment. An ozone generator positioned with respect to the compartment to selectively generate ozone is activated. The generated ozone is introduced into the compartment to treat the article. The level of ozone within the compartment is ramped to a first predetermined ozone concentration value. A rate of decline of the level of ozone within the compartment from the first ozone concentration value to a second predetermined ozone concentration value is detected with a sensing device positioned with respect to the compartment. The sensed rate of decline is compared to a predetermined rate of decline. The ozone generator is cycled between the first ozone concentration value and the second ozone concentration value if the sensed rate of decline is less than the predetermined rate of decline.

BRIEF DESCRIPTION OF THE DRAWINGS

FIG. 8 is a perspective sectional view of an exemplary regenerative dryer for the apparatus shown in FIG. 2.

FIG. 9 is a sectional view of another exemplary regenerative dryer for the apparatus shown in FIG. 2, the regenerative dryer including a valve in a first position.

FIG. 10 is a sectional view of the regenerative dryer shown in FIG. 9 with the valve in a second position.

FIG. 11 is a sectional view of the regenerative dryer shown in FIG. 9 taken generally along line 11-11 of FIG. 9.

FIG. 20 is a schematic illustration of another exemplary ozone conversion device for the apparatus shown in FIG. 2 with a damper in a first position.

FIG. 21 is a schematic illustration of the ozone conversion device shown in FIG. 13 with the damper in a second position.

FIG. 24 graphically illustrates an ideal cycle versus a stinky shirt cycle for a set period of time during an ozone generation/deodorizing cycle.

DETAILED DESCRIPTION

It should, of course, be understood that the description and drawings herein are merely illustrative and that various modifications and changes can be made in the structures disclosed without departing from the present disclosure. It will also be appreciated that the various identified components of the apparatus for disinfecting and/or deodorizing an article described herein are merely terms of art that may vary from one manufacturer to another and should not be deemed to limit the present disclosure. Like numerals refer to like parts throughout the several views.

Figure 1:
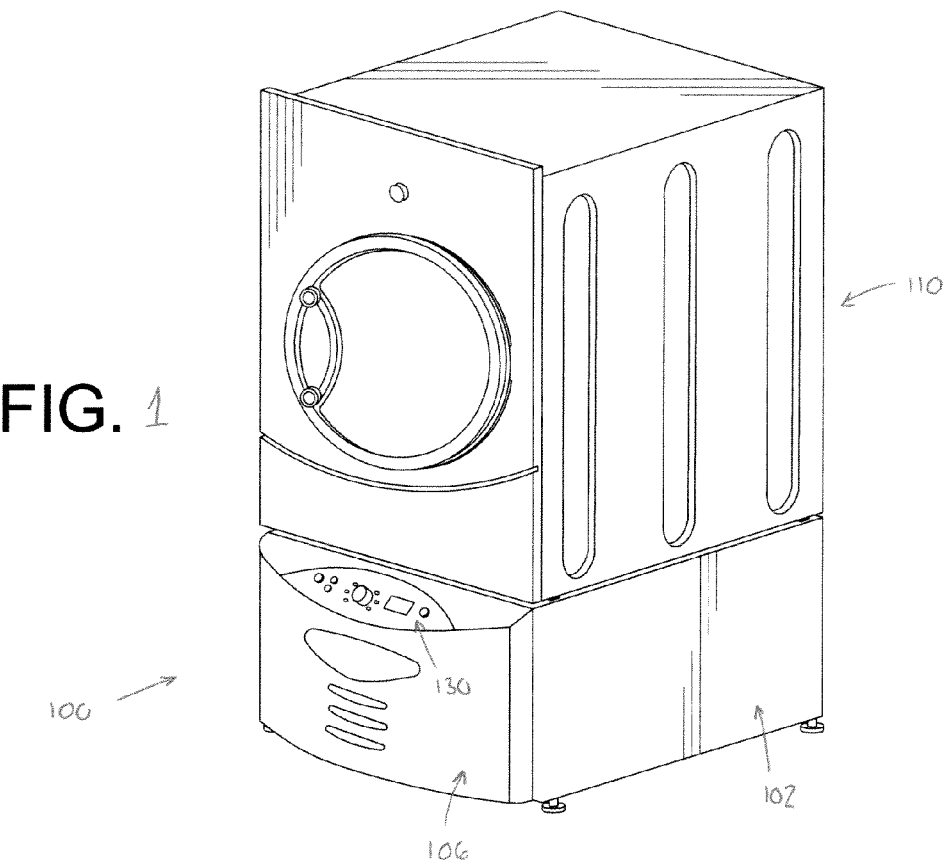
FIG. 1 is a front perspective view of an appliance including an exemplary disinfection and/or deodorization apparatus.
Figure 2:
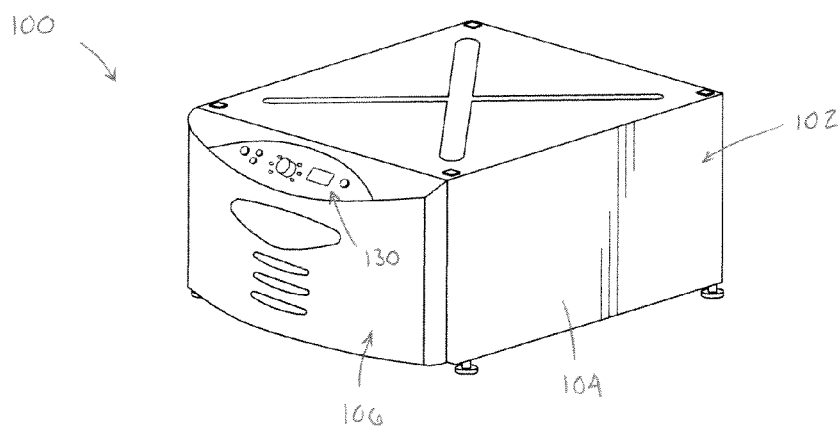
FIG. 2 is a front perspective view of the apparatus shown in FIG. 1 with a drawer in a closed position.
Figure 3:
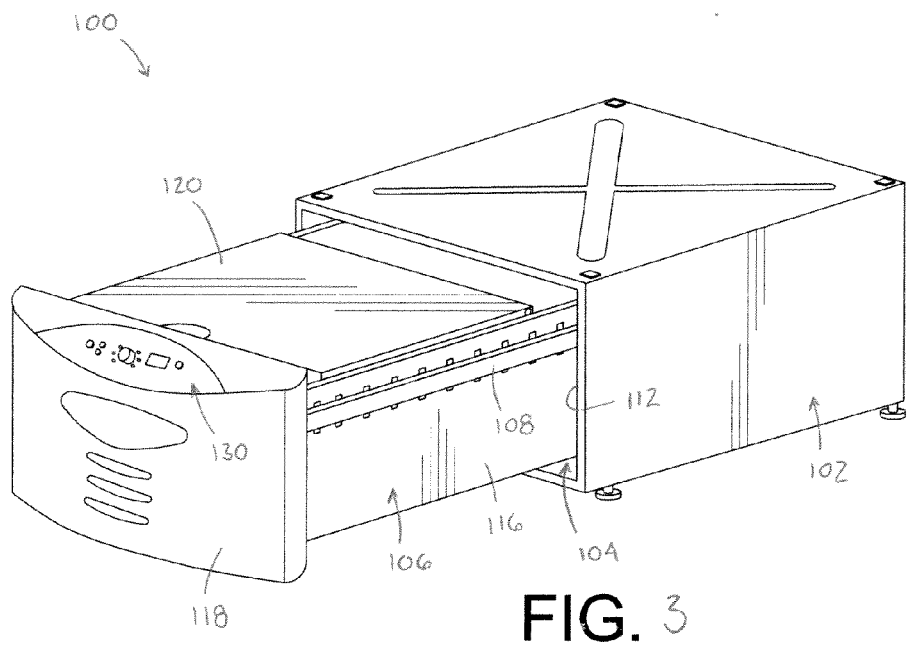
FIG. 3 is a perspective view of the apparatus shown in FIG. 2 with the drawer in an open position.
Figure 4:
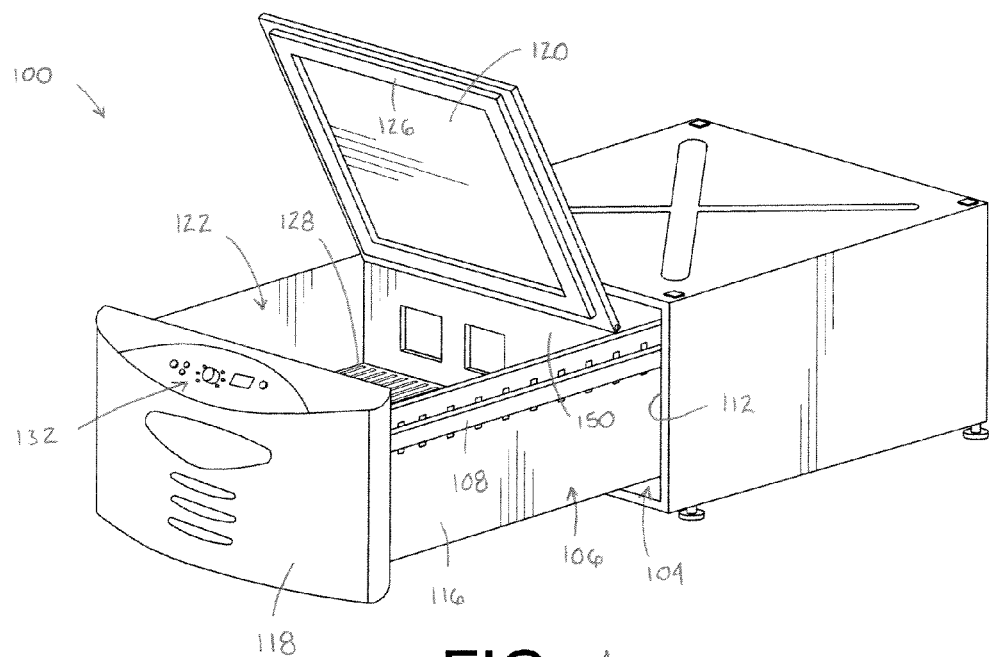
FIG. 4 is a perspective view of the apparatus shown in FIG. 3 with a drawer lid in an open position.

Referring now to the drawings wherein the showings are for purposes of illustrating one or more exemplary embodiments only and not for purposes of limiting the same, FIGS. 1-4 schematically illustrates an exemplary apparatus 100 for disinfecting and/or deodorizing an article. As illustrated, the apparatus 100 is positioned below a washing machine 110 as a pedestal; although, this is not required. It should be apparent that the apparatus 100 may be used in conjunction with any suitable home or industrial appliance, such as a dishwasher, a dryer and/or a dry cleaning machine. Further, in alternative embodiments, the apparatus 100 is suitable for use as a standalone home appliance. The apparatus 100 includes a chassis or cabinet 102 defining a compartment or chamber 104. A garment bin or drawer 106 is positioned within the chamber 104. In the exemplary embodiment, the drawer 106 is slidably positioned within the chamber and movable between a closed or retracted position, as shown in FIG. 2, and an open or extended position, as shown in FIGS. 3 and 4.

In the exemplary embodiment, the cabinet 102 can be made of any suitable ozone compatible material including, without limitation, a metal and/or a plastic material, such as a thermoplastic material including, without limitation, a polypropylene (PP), polyvinyl chloride (PVC) and/or polycarbonate (PC) material. In the depicted embodiment, the drawer includes a retracting mechanism, such as telescopic slide assemblies 108 mounted on opposing sides of the drawer. Alternatively, the drawer can be motorized to automatically move between the retracted position and the extended position. A gasket 112 can be provided between the cabinet 102 and the drawer 106. As such, the drawer is sealingly coupled to the cabinet in the retracted position to form a substantially air-tight seal therebetween.

With continued reference to FIGS. 3 and 4, the drawer 106 includes a drawer frame 116 coupled to a front panel 118, and a lid 120 pivotally coupled to the drawer frame to cover a compartment 122 defined within the drawer. Similar to the cabinet 102, the drawer frame 116 can be made of a suitable ozone compatible material. The lid 120 is coupled to drawer frame 116 by at least one hinge (not shown), and is movable between a closed position, as shown in FIG. 3, and an open position, as shown in FIG. 4, for inserting into or removing an article(s), such as a sweatshirt, shoes or a jacket, from the compartment 122. The hinge can be a self-standing hinge, such as a friction hinge, a spring-loaded hinge, a concealed hinge, or any suitable hinge that retains the lid 120 in any desired position without user manipulation. A gasket 126 can be provided on one of the drawer frame 116 and an inner surface of lid 120. As such, the lid is sealingly coupled to drawer frame in the closed position for cooperatively forming the substantially air-tight compartment 122. A shelf 128 can be positioned within the compartment 122 for supporting the article(s) to be treated. The shelf can be removable for cleaning, as desired.

The front panel 118 includes a controller 130 having a plurality of input selectors and/or a display 132 mounted on an outer surface of the front panel. The input selectors and/or display form a control interface for user selection of operation cycles and/or operation features. The display indicates the selected features and/or other items of interest to the user. The controller 130 is in operational control communication with the input selectors and/or display 132 for receiving from and/or sending to the input selectors and/or display 132 operational control signals. In the exemplary embodiment, the controller 130 is also operatively coupled to other apparatus components to facilitate executing operation cycles, as described in greater detail below (see FIGS. 22 and 23).

A lock 140 is operatively connected to the lid 120 and the controller 130. The lock locks or releases the lid in or from, respectively, the closed position in response to an ozone level within the compartment 122, as described in detail below. The lock may be a motorized latch controlled by the controller 130 or a magnetic lock controlled by an ozone sensing device or sensor 400 (see FIG. 5), described in greater detail below. A door interlock switch 144 is positioned with respect to the lid for detecting the position of the lid. Specifically, the door interlock switch is in operational communication with the controller 130 for detecting whether the lid 120 is in the closed position.

Figure 5:
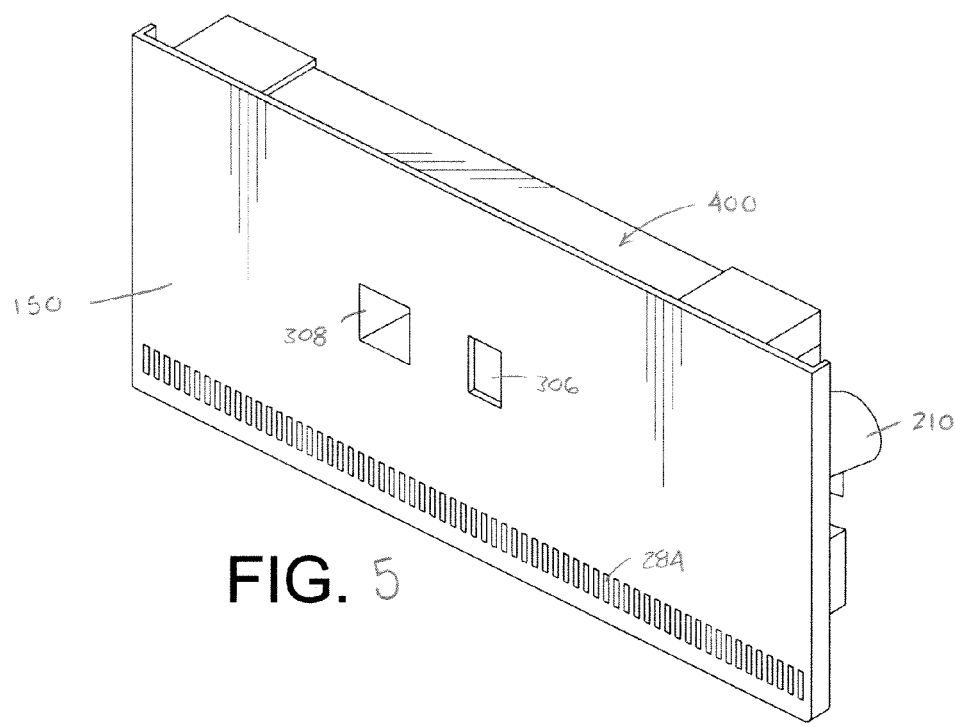
FIG. 5 is a perspective view of a plenum plate of the apparatus shown in FIG. 4.
Figure 6:
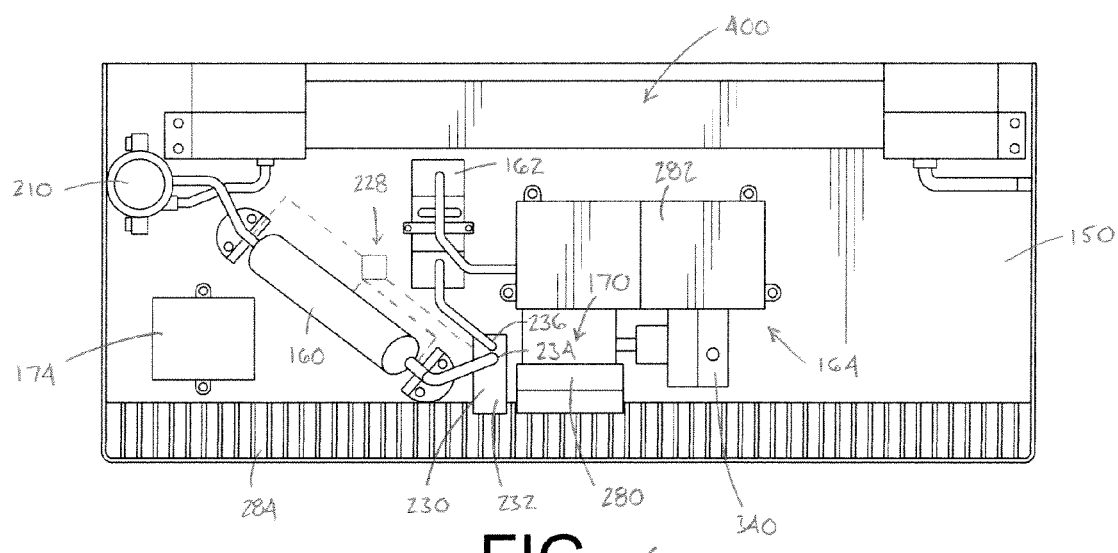
FIG. 6 is a rear elevational view of the plenum plate of FIG. 5 schematically illustrating the operational components of the apparatus shown in FIG. 2.
Figure 7:
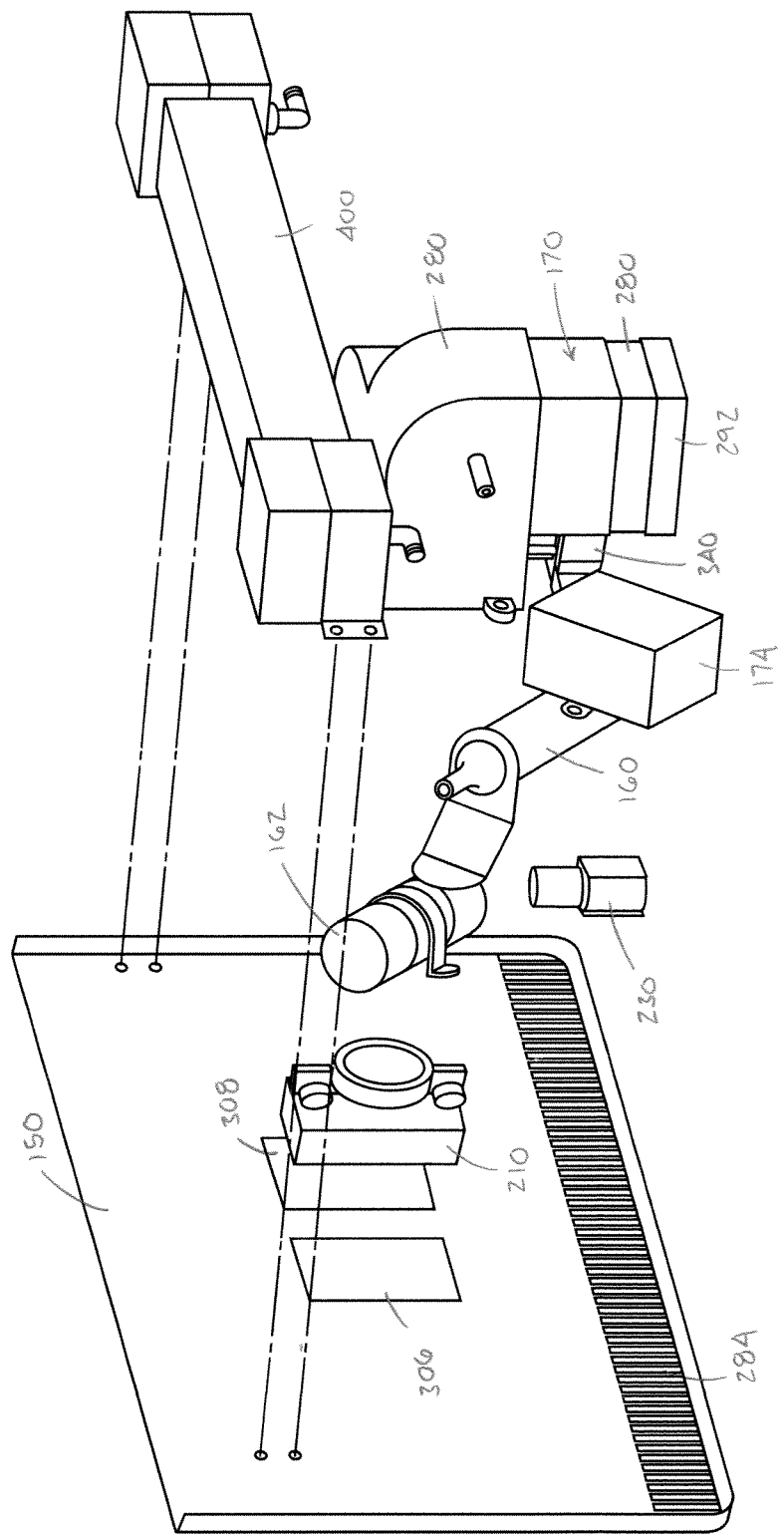
FIG. 7 is a partial exploded perspective view of FIG. 6.

With reference to FIGS. 5-7, a plenum plate or partitioning wall 150 of the drawer frame 116 separates the compartment 122 from the operational components of the apparatus 100. As shown, a regenerative dryer 160 is positioned with respect to the compartment 122 and is configured to dehydrate air flowing into an ozone generator 162. The use of the regenerative dryer takes advantage of the fact that dry air reacts better in the ozone generator 162, yielding better ozone concentration output, which, in turn, results in a better "kill rate" with respect to bacteria and stink/odor associated with an article placed within the apparatus 100. The ozone generator 162 is in communication with the regenerative dryer 160 and is positioned with respect to the compartment 122. The ozone generator is configured to selectively generate ozone. In one embodiment, the ozone generator includes a corona discharge ozone generator or an ultraviolet lamp for producing ozone, such as a 185 nm ultraviolet lamp. The generated ozone is introduced into the compartment via an air handler assembly 164. An ozone conversion device 170 is positioned with respect to the compartment 122 and is configured to selectively convert ozone to oxygen. The controller 130 is configured to selectively activate the dryer, ozone generator and ozone conversion device. A power generator 174 is provided for providing high voltage to the operational components of the apparatus 100.

With reference to FIG. 8, the regenerative dryer 160 includes a housing 180 having an air inlet 182 and an air outlet 184 located downstream from the air inlet. The air inlet 182 of the dryer is in communication with an air pump 210, which can be mounted to the plenum plate 150. The air outlet 184 is in communication with the ozone generator 162. In the depicted exemplary embodiment, the housing 180 is generally cylindrical in shape; however, it should be appreciated that the housing can have alternative conformations. For example, the housing 180 can have an oval conformation to lessen a thickness of the dehydrating agent contained therein for faster regeneration. The housing defines a chamber 186. A desiccant or dehydrating agent 190 is disposed within the chamber for absorbing moisture laden in the air. After a predetermined number of cycles, depending on the relative humidity of air and volume of dehydrating agent used, the dehydrating agent needs to be regenerated. The dehydrating agent is operatively regenerated by heat for vaporizing and removing moisture in the dehydrating agent when saturated with the moisture. The humid air is then exhausted, providing protection of the ozone producing system.

The housing includes a pair of end caps 200, 202, one end cap for each of the air inlet 182 and the air outlet 184 of the housing. As shown, the end caps are generally funnel-shaped; although, it should be appreciated that the shape of the end caps is generally dependent on the conformation of the housing 180. Each end cap 200 and 202 is a separate component which is securely attached to the housing 180. Each end cap can be made from spun copper; although, this is not required. The regenerative dryer 160 further includes a first filter 212 located downstream of the air inlet 182 and a second filter 214 located upstream of the air outlet 184. The dehydrating agent 190 is disposed between the first and second filters. The first and second filters filter dirt from the airstream flowing through the regenerative dryer 160. The first filter can be a coarse filter for trapping dust particles. The second filter can be a fine mesh filter and can comprise a pleated filter material and can be an electrostatic or high-efficiency particulate arresting (hepa) grade filter, which is capable of trapping very small dust particles.

The dehydrating agent 190 can be selected from silica gel granules, calcium carbonate granules or any other water-absorbable materials. Aluminum silica ($SiO_2$) is generally used as a dehydrating agent since it has been found to be non-carcinogenic to humans. After being saturated with moisture in the dehydrating agent 190, heat is applied to vaporize the moisture from the dehydrating agent so that upon removal of water from the dehydrating agent, the dehydrating agent is regenerated ready for next dehydration or dehumidification. To this end, the dryer 160 further includes a heater 220 for regenerating the dehydrating agent. In the depicted exemplary embodiment, the housing 180 is formed of a heat conductive material (e.g., copper tubing) and the heater 220 at least partially surrounds an outer surface of the housing. The heater can have a sleeve-like configuration and defines an elongated aperture dimensioned to receive therein at least a portion of the housing. The heat generated by the heater radiates through the housing 180 towards the dehydrating agent 190 to heat the moisture-saturated dehydrating agent for regenerating the dehydrating agent. The heater 220 can be configured as an electric heating element; although, it should be appreciated that that alternative heaters for heating the dehydrating agent 190 are contemplated. For example, the dryer heater 220 can be a positive temperature coefficient heater which is configured to limit temperature of the heater to a maximum desired regenerative temperature.

According to the exemplary embodiment, in order to detect when the dehydrating 190 requires reactivation a sensing device 228 (FIG. 6) can be provided. The sensing device 228 is configured to measure the humidity of the air before entering the regenerative dryer 160 and after exiting the regenerative dryer. When the change in humidity becomes relatively small, the dehydrating agent 190 would require regeneration. The sensing device 228 can be operatively connected directly to the heater 220 such that when the sensing device detects a relatively small humidity change, the heater will be actuated. Alternatively, the sensing device can communicate with the controller 130. When the change in humidity becomes relatively small, the controller actuates the heater 220 to regenerate the dehydrating agent 190.

An air handler valve mechanism 230 is operatively connected to the regenerative dryer 160. As shown in FIG. 6, the valve mechanism 230 includes a housing 232 having an inlet port 234, an outlet port 236 and an exhaust port (not visible). The inlet port is in communication with the air outlet 184. The outlet port is in communication with the ozone generator 162. A valve, such as a solenoid valve, is positioned in the housing to selectively allow airflow through one of the outlet port and exhaust port. During ozone generation, the exhaust port is closed by the valve and air flows through the outlet 236 to the ozone generator 162. The valve is actuated during the regeneration of the dehydrating agent 190 to exhaust moisture from the dehydrating agent through the exhaust port to atmosphere. It should be appreciated that in addition to or instead of monitoring humidity, the controller 130 can be configured to activate the heater 220 after a predetermined number of cycles of ozone generation to regenerate the dehydrating agent 190.

With reference to FIGS. 9-11, a regenerative dryer 240 according to another exemplary embodiment is shown. The regenerative dryer includes a housing 242 having an air inlet 244 and an air outlet 246 located downstream from the air inlet. The housing defines a chamber 250. A dehydrating agent 252 is disposed within the chamber 254 for absorbing moisture laden in the air. The dehydrating agent is operatively regenerated by heat for vaporizing and removing moisture in the dehydrating agent when saturated with the moisture. The housing 242 further includes an exhaust port 256 for releasing the moisture captures by the dehydrating agent 250. An air handler valve mechanism 260 is operatively connected to the housing 242.

The valve mechanism 260 includes a piston 262 and a solenoid 264 for displacing the piston between a first position (FIG. 9) and a second position (FIG. 10). In the exemplary embodiment, the piston 262 can be formed of a magnetic material so that the piston is displaced when the solenoid is powered. The solenoid 264 can be a coil which is wound at least partially around the piston. Energization of the coil moves the piston from the first position to the second position. In the first position, the piston is spaced from the air outlet 246 to allow dehydrated air to flow from the regenerative dryer 240 to the ozone generator 162. The piston closes the exhaust port 256. In the second position, the piston 262 is spaced from the exhaust port 256 to allow for exhausting of vaporized moisture from the dehydrating agent 252. The piston closes the air outlet 246. A bias mechanism 270 (such as a spring) urges the piston towards the first position. The bias mechanism is compressed by the piston 262 in the second position. As shown, the bias mechanism at least partially surrounds the piston 262. The dryer 240 further includes a heater for regenerating the dehydrating agent 252. In this embodiment, the heat generated from the energization of the solenoid coil increases the temperature of the dehydrating agent 252 thereby releasing the moisture captured therein through the exhaust port 256. It should be appreciated that an auxiliary heater (not shown) can be provided to further increase the temperature of the dehydrating agent 252 to release the water captured therein.

Figure 12:
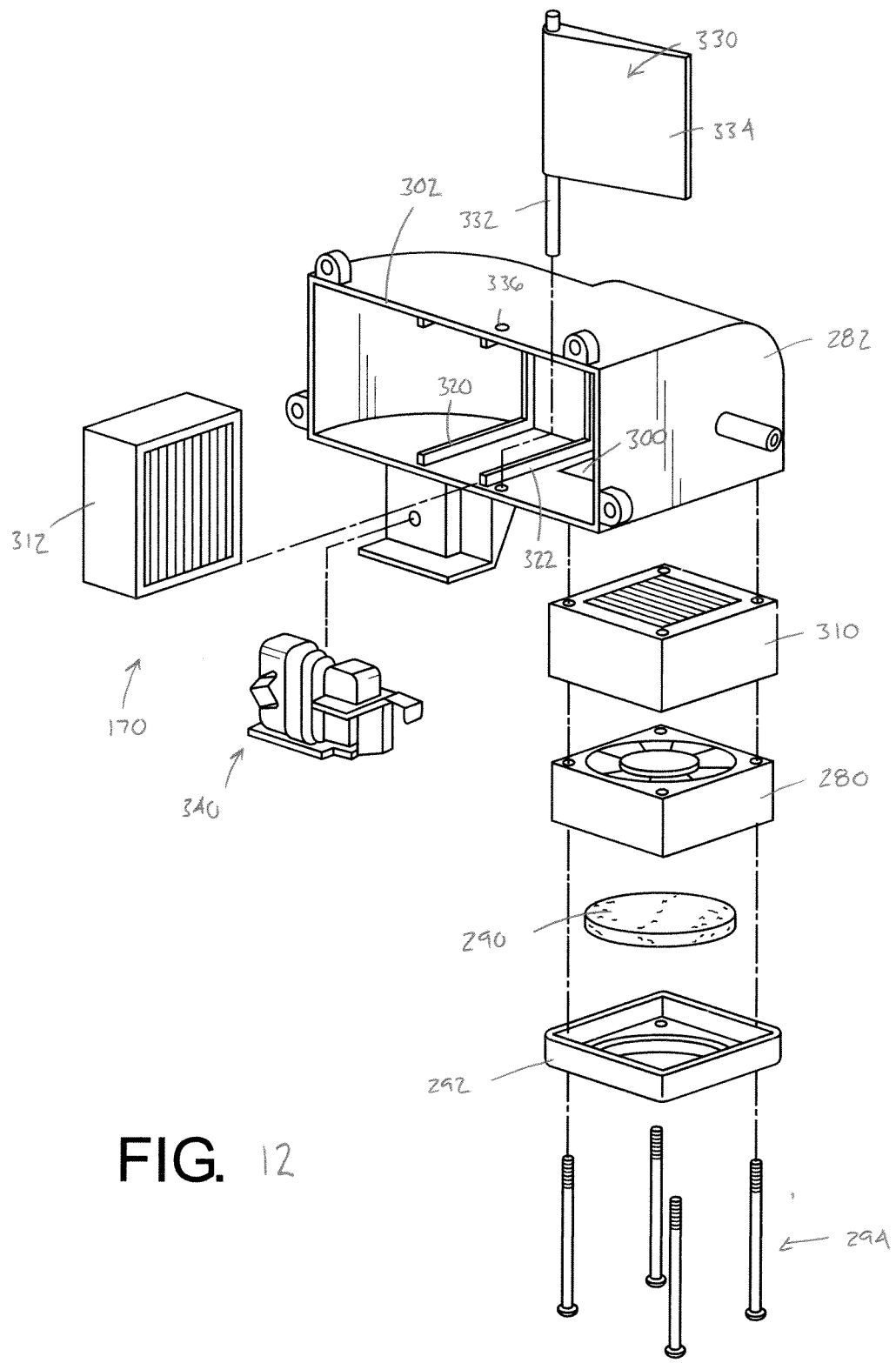
FIG. 12 is an exploded perspective view of an exemplary air handler assembly for the apparatus shown in FIG. 2.

With reference to FIG. 12, the air handler assembly 164 includes a circulation fan 280 connected to a plenum or housing 282. The fan 280 is positioned with respect to the compartment 122 to direct an airflow through the compartment. As shown in FIG. 7, a plurality of vents 284 are defined through the plenum plate 150 to facilitate the airflow between the compartment 122 and the fan 280. An air filter 290 is provided at an air inlet of the fan 280 to remove dust particles from the air. The air filter is housed in a housing 292 which is releasably connected to the fan 280 via conventional fastening means, such as the illustrated bolts 294. This allows the air filter 290 to be removed and replaced, if desired. As shown, the bolts releasably attach the circulation fan to the housing. The plenum 282 includes an air inlet 300 and an air outlet 302. The plenum is coupled to the plenum plate 150 such that the air outlet 302 is in selective communication with one of first and second openings 306 and 308, respectively, located on the plenum plate depending upon the operating mode as hereinafter described.

As shown in FIG. 12, the ozone conversion device 170 is connected to the housing 282 and is configured to reduce the ozone within the compartment 122. It is contemplated that the ozone conversion device 170 includes at least one of a heater and a catalyst. In the depicted embodiment of FIG. 12, the ozone conversion device includes a heater 310 and a catalyst 312. The fan 280 is operatively positioned with respect to the catalyst 312 to facilitate converting ozone into oxygen. The heater 310 is located downstream of the fan 280 and upstream of the inlet 300 of the housing 282. The heater can be releasably attached to the housing 282 via the bolts 294. Heat generated from the heater 310 removes residual ozone smell left in the article within the compartment 122 after the ozone generation/deodorizing cycle. The catalyst 312 is positioned within the housing 282 downstream of the inlet 300. As shown, the housing 282 includes a pair of guides 320 and 322 having a generally U-shaped conformation. The guides are spaced apart such that the catalyst can be slidingly received within the housing 282 between the guides 320 and 322. The allows the catalyst to be easily removed from the housing 282, if desired. Catalyst material may include, without limitation, a manganese compound, an active carbon and/or any suitable catalyst material known to those skilled in the art. A damper 330 is operatively coupled to the housing 282. The damper includes a post 332 and a door 334 connected to the post. The post is received in corresponding apertures 336 located on the housing 282 such that the door is movable within the housing 282. The door 334 is configured to block airflow through the catalyst 312 in a first position (FIG. 13) and block the portion of the outlet 302 upstream of the catalyst 312 in second position (FIG. 15) to direct air through the catalyst. A door mechanism 340 is connected to the housing and is configured to rotate the post 332 such that the door 334 moves between the first and the second position.

Figure 13:
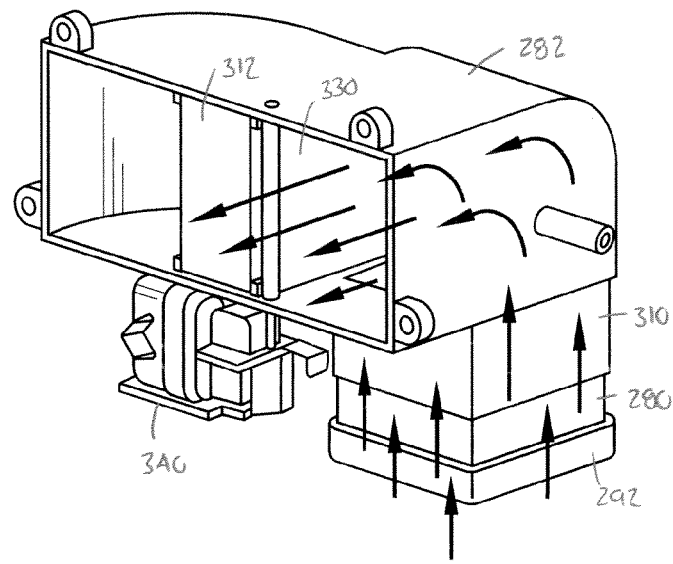
FIG. 13 is a perspective view of the air handler assembly shown in FIG. 12 with a damper in an open position.
Figure 14:
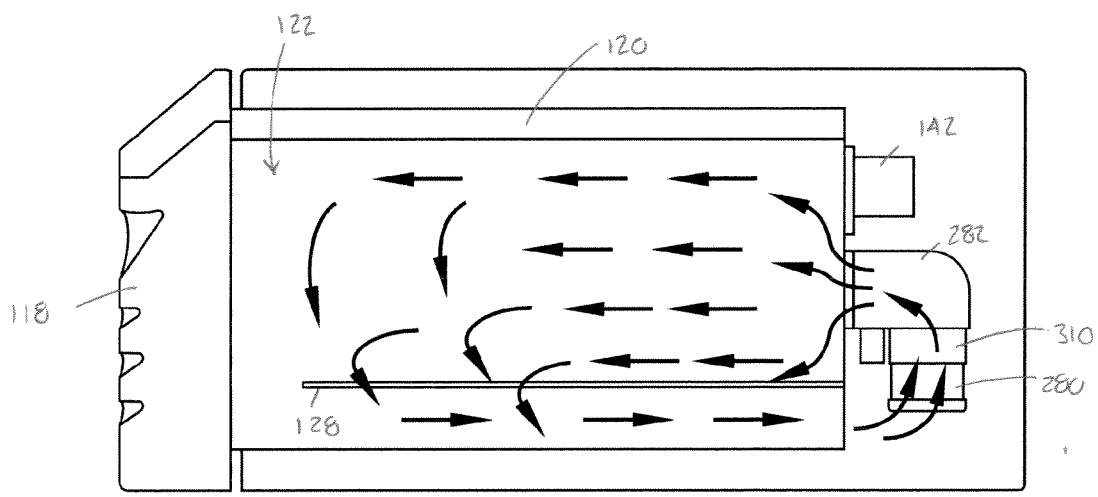
FIG. 14 is schematic illustration of the apparatus shown in FIG. 2 showing the airflow through the apparatus during an ozone generation/deodorizing cycle.
Figure 15:
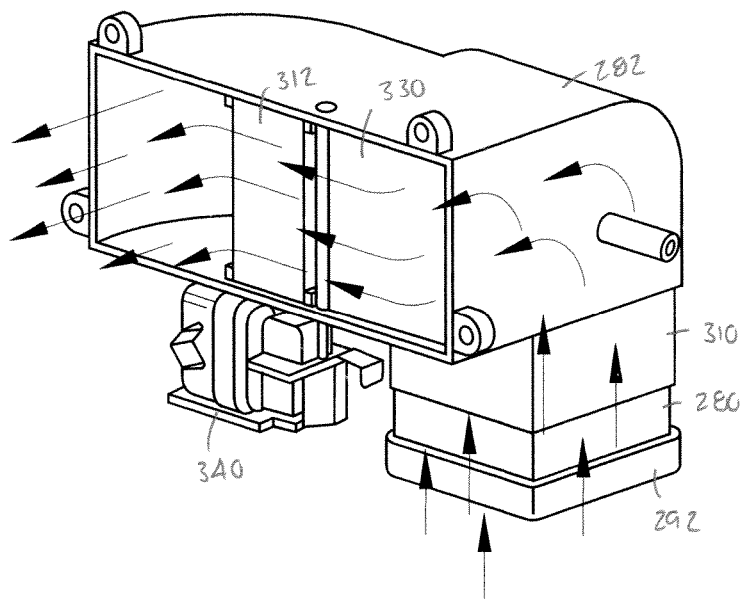
FIG. 15 is a perspective view of the air handler assembly shown in FIG. 12 with the damper in an closed position.
Figure 16:
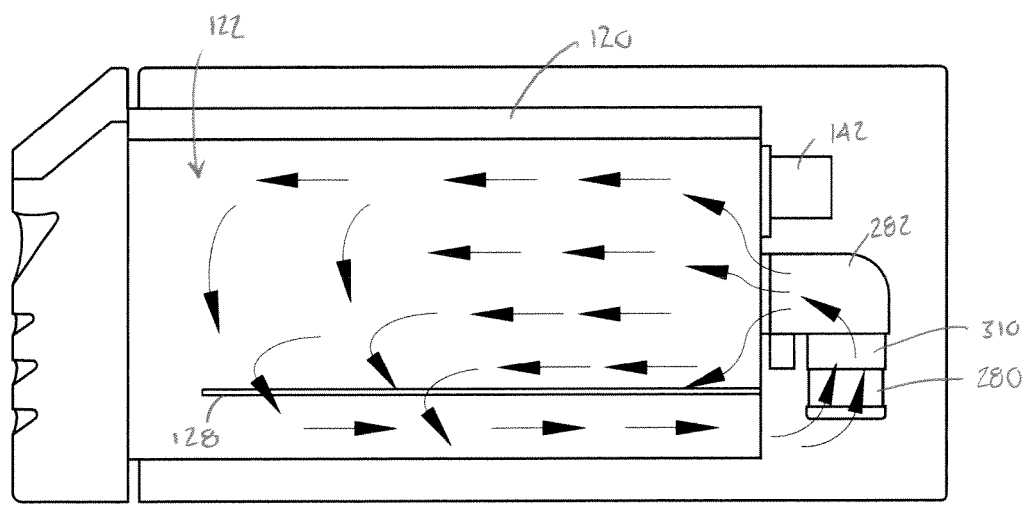
FIG. 16 is a schematic illustration of the apparatus shown in FIG. 2 showing the airflow through the apparatus during an ozone/residual ozone kill cycle.

As shown in FIGS. 13 and 14, in a first airflow mode (i.e., during the ozone generation/deodorizing cycle), the door 330 is in the first position such that the door abuts the guide 322. This prevents the flow of ozone enriched air through the catalyst 312. The fan 280 circulates generated ozone through the compartment 122. Particularly, the fan directs the ozone enriched air through the heater, which is not actuated, the housing 282, the first opening 306 in the plenum plate 150 and into the compartment 122. The air bypasses the catalyst 312. As shown in FIGS. 15 and 16, in a second airflow mode (i.e., during the ozone/residual ozone kill cycle), the door 330 is in the second position such that the door closes a portion of the air outlet 302. The fan 280 directs the ozone enriched air through the heater 280 and the catalyst 312 to facilitate converting ozone into oxygen. The air flows out of the housing 282, the second opening 308 in the plenum plate and into the compartment. Actuation of the heater 310 further facilitates the converting of ozone to oxygen.

Figure 17:
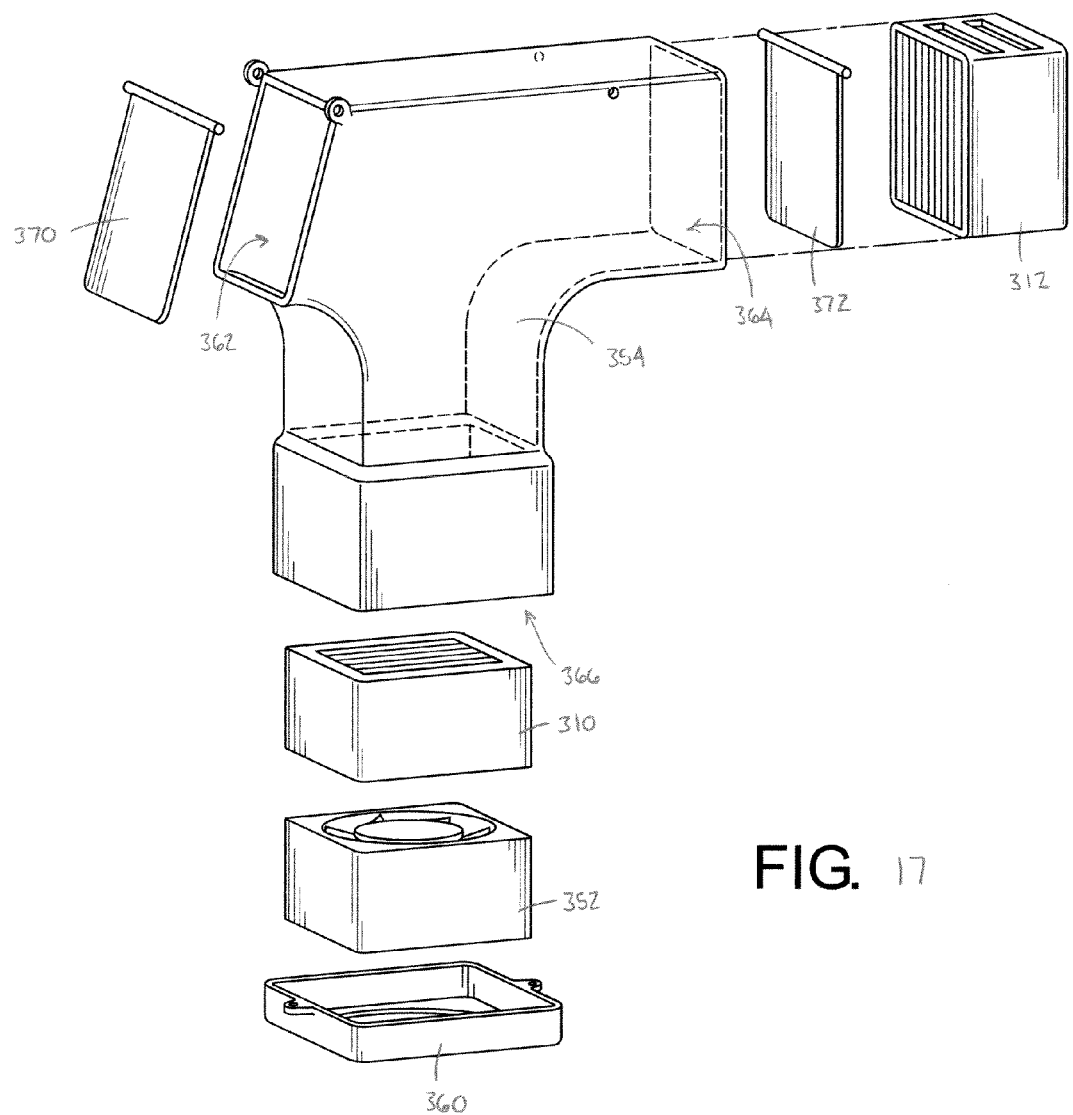
FIG. 17 is an exploded perspective view of another exemplary air handler assembly for the apparatus shown in FIG. 2.

With reference to FIG. 17, an air handler assembly 350 according to another exemplary embodiment is illustrated. The air handler assembly 350 includes a reversible circulation fan 352 connected to a plenum or housing 354. An air filter (not shown) can be provided at an air inlet of the fan 352 to remove dust particles from the air. The air filter can be housed in a fan housing 360 which is releasably connected to the fan 352 via conventional fastening means. The plenum 354 includes an air outlet 362, an air inlet 364 and an opening 366 configured to at least partially receive the fan 352. The plenum is connected to the plenum plate 150 such that the air outlet 362 is in selective communication with the first opening 306 and the air inlet 364 is in selective communication with the second opening 308. The heater 310 and catalyst 312 of the ozone conversion device 170 are connected to the housing 354. Particularly, the heater 310 is positioned within the opening 366 and the catalyst 312 is positioned within the air inlet 364. The fan 352 is operatively positioned with respect to the heater 310 and catalyst 312 to facilitate converting ozone into oxygen. Heat generated from the heater 310 removes residual ozone smell left in the article within the compartment 122 after the ozone generation/deodorizing cycle. A first check valve 370 is provided at the air outlet 362 and a second check valve 372 is provided at the air inlet 364. Each check valve 370, 372 is pivotally connected to the housing 354.

Figure 18:
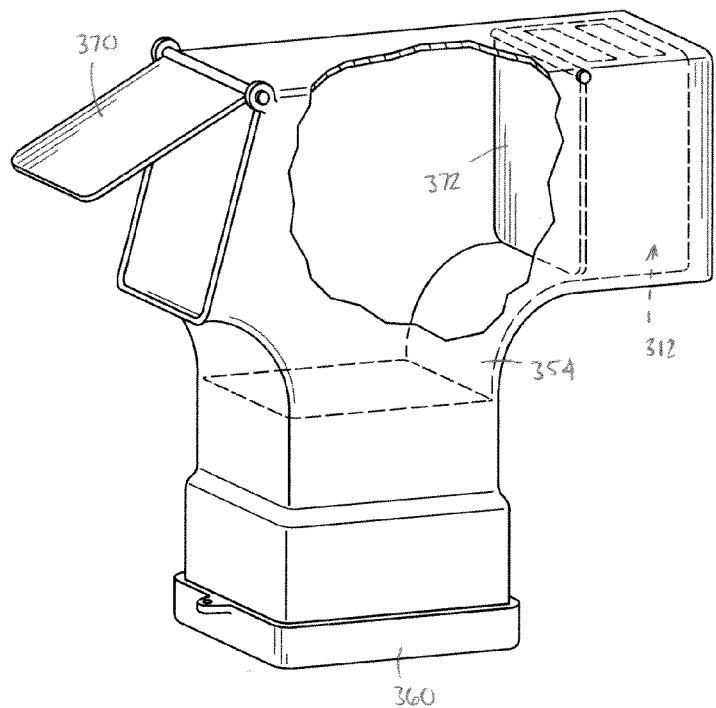
FIG. 18 is a perspective view of the air handler assembly of FIG. 17 in a first airflow mode.
Figure 19:
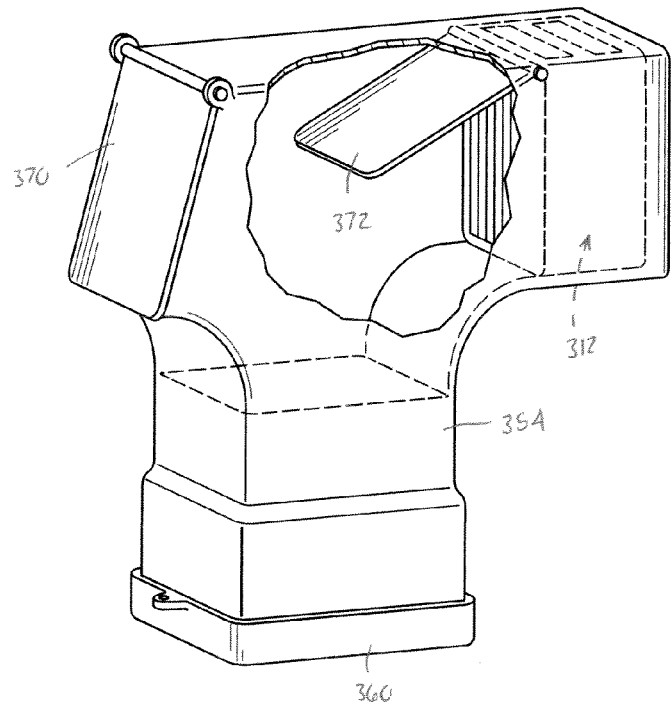
FIG. 19 is a perspective view of the air handler assembly of FIG. 17 in a second airflow mode.

In a first airflow mode (i.e., during the ozone generation/deodorizing cycle), the circulation fan 352 draws air into the housing opening 366, through the air outlet 362 and into the compartment 122. As shown in FIG. 18, the first check valve 370 is in an open position and the second check valve 372 is in a closed position to prevent the flow of ozone enriched air through the catalyst 312. As shown in FIG. 19, in a second airflow mode (i.e., during the ozone/residual ozone kill cycle), the first check valve 370 is in a closed position to close the air outlet 362 and the second check valve 372 is in an open position. The circulation fan 352 is reversed to draw ozone enriched air into the air inlet 364, through the catalyst 312 and heater 310 and out of the housing opening 366. The air flows out of the housing 354 and into the compartment 122. Actuation of the heater 310 further facilitates the converting of ozone to oxygen. More specifically, during the ozone generation/deodorizing cycle, circulation fan 352 creates high pressure in the housing 354 thereby drawing air into housing 354 through opening 366, air exiting the housing 354 through opening 362. The high pressure opens the first check valve 370 and closes the second check valve 372. Conversely, during the ozone/residual ozone kill cycle, the fan 352 is reversed creating low pressure in the housing 354 thereby drawing air into the housing 354 through the air inlet 364. The low pressure closes the first check valve 370 and moves the second check valve 372 to an open position. Air exits from the housing 354 via the opening 366.

With reference to FIGS. 20 and 21, an ozone conversion device 380 for use with the apparatus 100 according to another exemplary embodiment is schematically illustrated. In this embodiment, the ozone conversion device includes a housing 382 for housing at least one of a heater 384 and a catalyst 386 located on a damper 388. A circulation fan 390 is connected to the housing for directing airflow through the housing to the compartment 122. The damper including the catalyst is configured to be pivoted in front of the heater. In a first airflow mode (i.e., during the ozone generation/deodorizing cycle), the damper and catalyst is in a first position relatively remote from the heater and out of the air flow path though the housing 382 (FIG. 20). The heater is not actuated. The fan 390 circulates ozone enriched air through the housing 382 and the compartment 122. In a second airflow mode (i.e., during the ozone/residual ozone kill cycle), the damper and catalyst is in a second position relatively close to the heater 384 and in the air flow path (FIG. 21). The heater 384 is actuated. The fan 390 directs the ozone laden air within the compartment 122 through the catalyst 386 and heater 384 to facilitate converting ozone into oxygen.

With reference again to FIGS. 6 and 7, an ozone sensing device 400 is positioned with respect to the compartment 122 and is configured to detect a level of ozone within the compartment and generate a signal representative of the level of ozone. In the exemplary embodiment, the ozone sensing device 400 includes a UV light emitting diode and uses the Beer-Lambert law to detect ozone concentration levels within the compartment 122. Although, it should be appreciated to one skilled in the art that alternative ozone sensing devices are contemplated. The controller 130 is in signal communication with the ozone sensing device 400 and is configured to operate one of the ozone generator 162 and ozone conversion device 170 in response to the signal transmitted from the ozone sensing device 400. It should be appreciated that the first apparatus 100 can also include the humidity sensor (as described above), a differential pressure sensor and/or a perfumer positioned therein. The humidity sensor detects the moisture content within the compartment 122, and the differential pressure sensor detects the pressure within the compartment 122. The humidity sensor and pressure sensor are in signal communication with the controller 130. The perfumer is used to introduce perfume into the compartment 122, as desired, and is in operational control communication with the controller 130. It should also be appreciated that the humidity sensor, differential pressure sensor and/or perfumer may be located at any suitable position within the apparatus to realize the desired functions.

Figure 22:
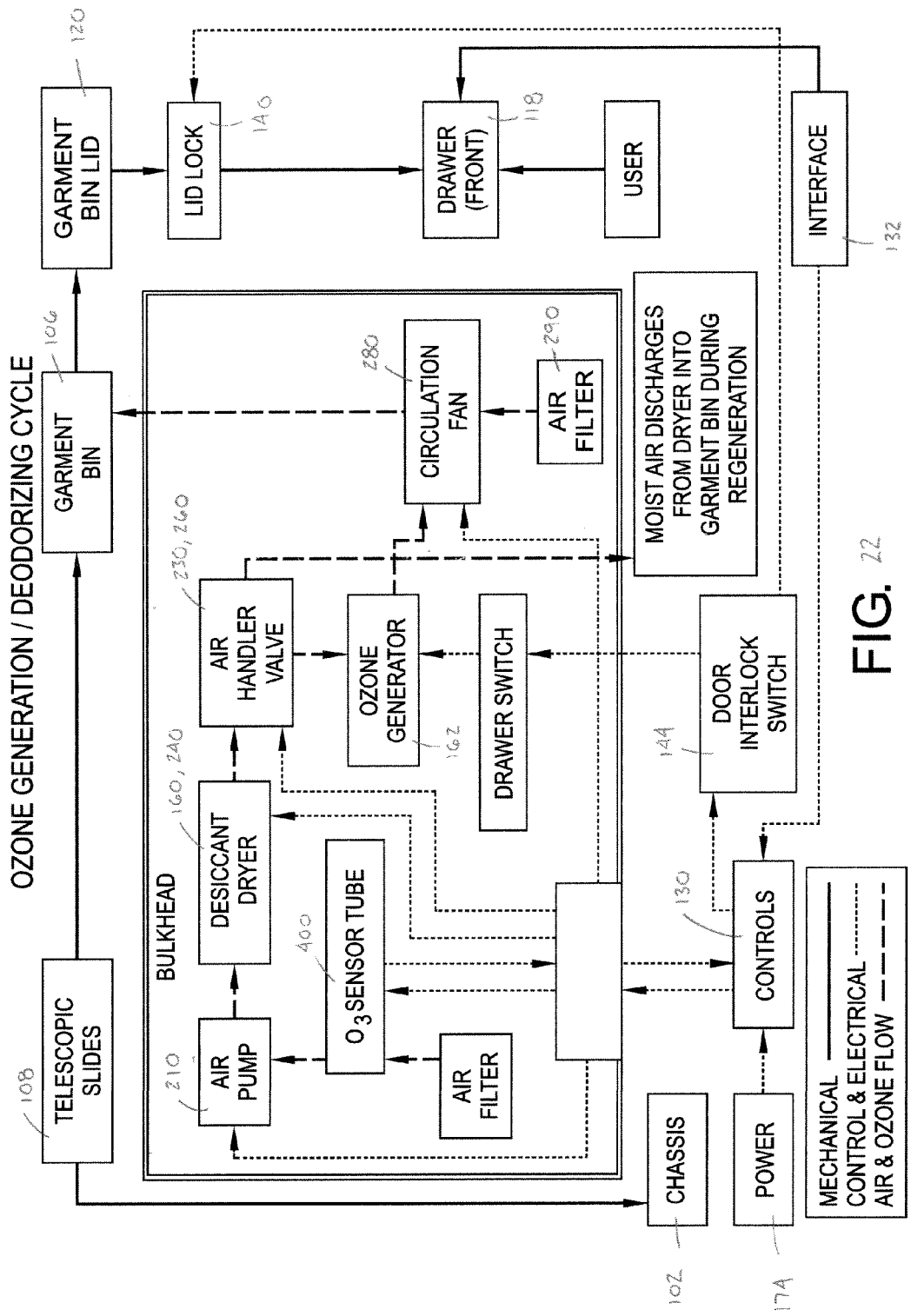
FIG. 22 illustrates the exemplary ozone generation/deodorizing cycle for the apparatus shown in FIG. 2.

In an exemplary disinfection/deodorizing cycle of the apparatus 100, as shown in FIG. 22, a user places an article within the compartment 122. The user inputs a load type, including a size and/or a type of material for the article. The user also can input a desired disinfection treatment level, such as heavy, medium or low. The controller 130 then determines a desired ozone dosage level and a treatment time based on the initial level of ozone, the treatment level and/or the load type. The controller 130 initiates the ozone generation/deodorizing cycle upon the door interlock switch 144 detecting that the lid 120 is in the closed position. The controller operates the lock 140 to lock the lid in the closed position. The air pump 210 directs air through the desiccant dryer 160 and into the ozone generator 162. The ozone generator creates ozone and the circulation fan 280 directs the generated ozone into the garment bin 106. The ozone flows across and/or through the articles within the compartment 122 to remove from the article undesired odors and/or to destroy through oxidation microorganisms, such as bacteria, viruses and/or fungi. Air within the compartment 122 is circulated through the compartment via the circulation fan 280.

Figure 25:
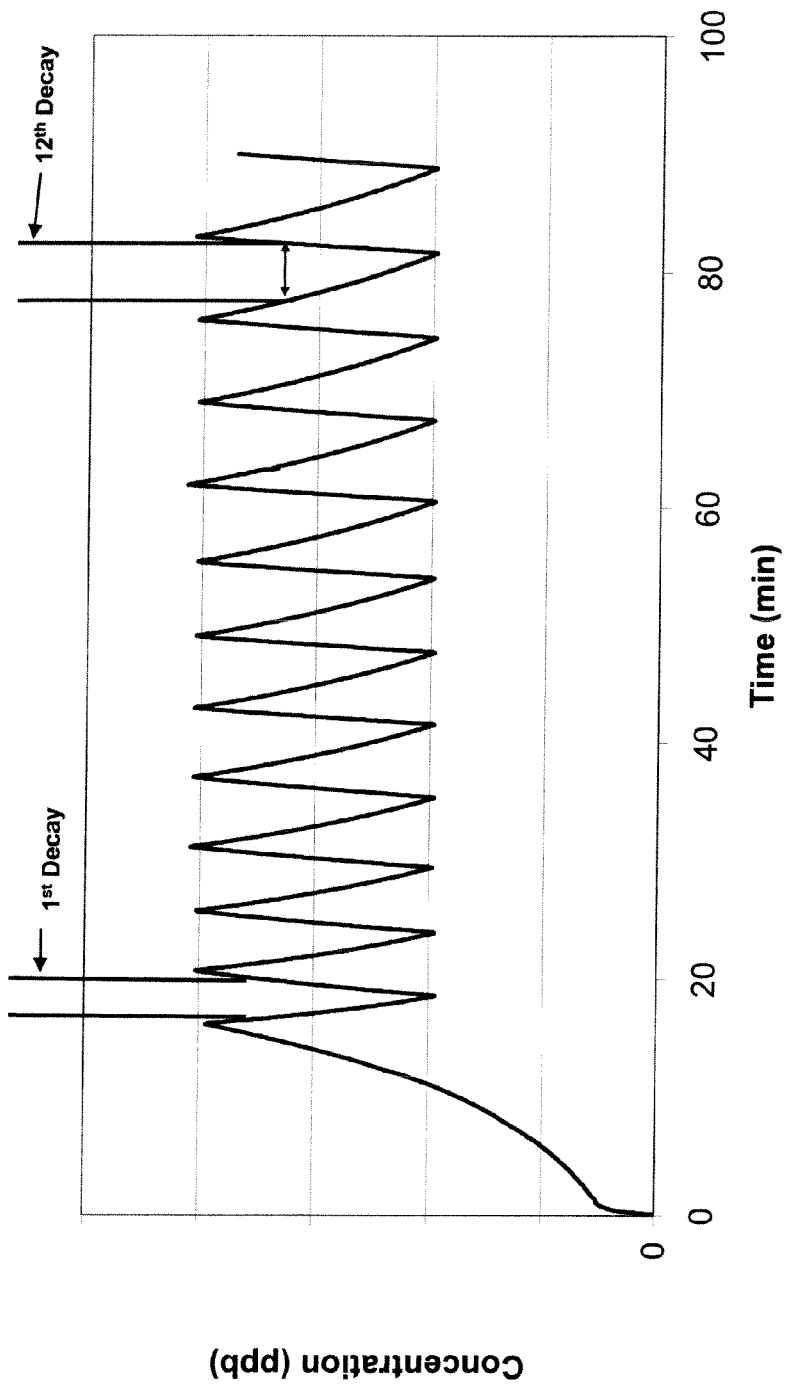
FIG. 25 graphically illustrates ozone concentration versus time during an ozone generation/deodorizing cycle.

According to one exemplary embodiment, the controller is configured to cycle the ozone generator 162 between a first predetermined ozone concentration value (e.g., about 18000 ppb to 22000 ppb) and a second predetermined ozone concentration value (e.g., about 8000 ppb to about 12000 ppb). The ozone generator 162 is energized until the first concentration value is detected, then de-energized until the second concentration value is detected, and again energized until the first concentration value is detected. The sensing device 400 is configured to monitor the rate of the decline of the ozone level (i.e., the rate of decay of the ozone) within the compartment 122 from the first ozone concentration value to the second ozone concentration value. As is graphically illustrated in FIGS. 24 and 25, the rate of decay of ozone during an ideal cycle takes a longer period of time than the rate of decay of ozone for a contaminated (i.e. stinky) article within the compartment 122. However, over successive cycles, as odor causing contaminates are gradually removed from the article, the rate of decay of ozone approaches to the ideal rate of decay. A rate of decay approximately equal to the ideal rate of decay indicates that the article within the compartment 122 is sufficiently clean. The controller 130 is configured to compare the sensed rate of decay to a predetermined rate of decay, such as the rate of decay of the ideal cycle graphically illustrated in FIG. 24, and to continue the cycling of the ozone generator 162 at least until the sensed rate of decay is approximately equal to the predetermined rate of decay.

The controller 130 is configured to compare the sensed rate of decay between successive cycles to determine a level of odor and/or bacteria remaining in the article. If the sensed rate of decay of ozone between the successive cycles is still less than the predetermined rate of decay, the controller is configured to again cycle the ozone generator between the first ozone concentration value and the second ozone concentration value. As is graphically illustrated in FIG. 24, the controller 130, by measuring the rate of decay of the ozone within the compartment 122, can determine if the article within the compartment is cleaned. Through successive cycling of the ozone generator 162, the rate of decay of the ozone within the compartment 122 is longer, which indicates that the undesired odors and/or microorganisms within the article are removed. Accordingly, the controller 130 continuously energizes or de-energizes the ozone generator 162 until the sensed rate of decay is approximately equal to the predetermined rate of decay. At that time, in the illustrated embodiment, the controller is configured to stop further ozone generation and end the disinfection/deodorizing cycle. However, it should be appreciated that the controller 130 can be configured to continue ozone generation for an additional period of time for increased assurance of the decontamination of the article.

It should also be appreciated that the ozone generation can be time based. For example, the controller 130 can control an operating time for the ozone generator 162, a temperature within the compartment 122 and/or a speed of the circulation fan 280 to maintain a desired ozone level within the compartment 122 for a predetermined period of time. At the end of the predetermined time period, the controller 130 ends the disinfection/deodorizing cycle and begins the ozone/residual ozone kill cycle regardless if the article within the compartment 122 is cleaned.

Figure 23:
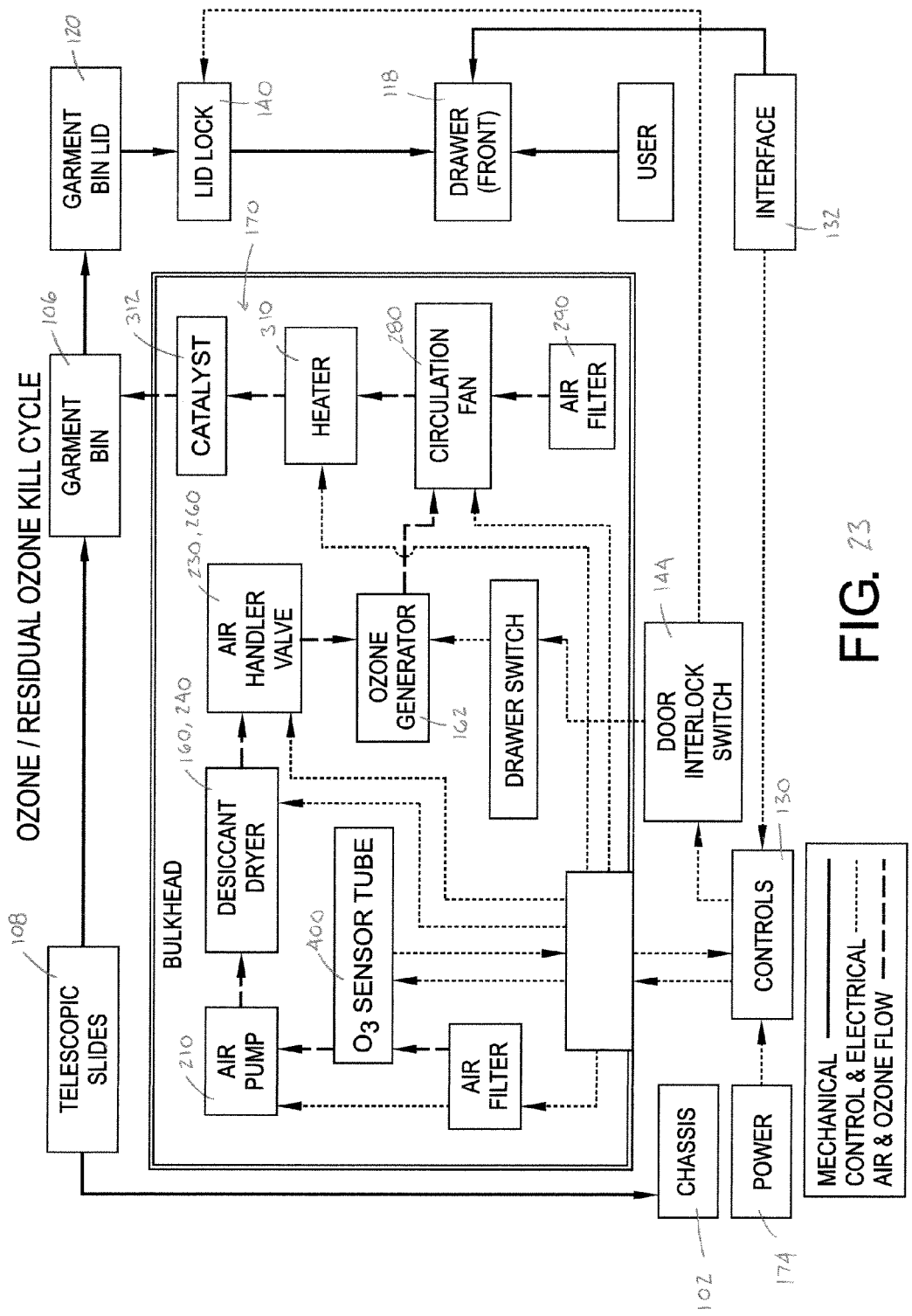
FIG. 23 illustrates the exemplary ozone/residual ozone kill cycle for the apparatus shown in FIG. 2.
Figure 2A:
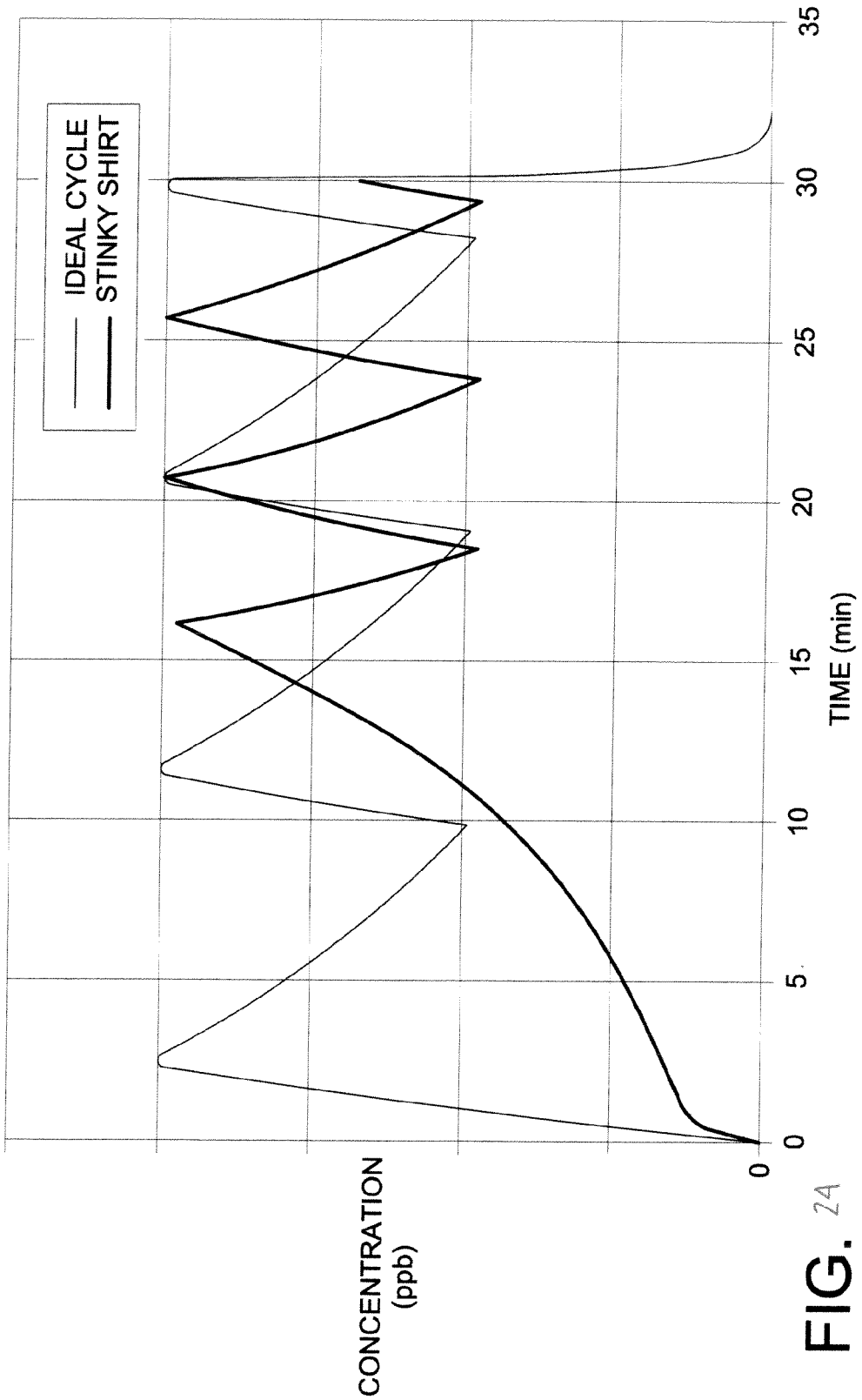

With reference to FIG. 23, at the end of the deodorizing process, the controller 130 de-energizes the ozone generator 162 and energizes the ozone conversion device 170 to complete the process. More specifically, the circulation fan 280 is energized to circulate air within the compartment 122 through the heater 310 and the catalyst 312. The heater is activated to facilitate converting ozone to oxygen. The ozone sensing device 400 detects whether ozone in the compartment 122 is reduced to a selected safe or threshold value. During this process, the damper 330 is moved to its second position such that the air flowing through the actuated heater 310 is directed through the catalyst and into the compartment through opening 308. The heat generated from the heater flows into the compartment 122 and removes any residual ozone smell left in the article.

The lid lock 140 maintains the lid 120 in the closed position until the detected ozone is reduced to a safe level. As such, the door 106 restricts ozone from exiting or escaping the apparatus 100 during operation. Lock 140 unlocks the lid 120 in response to a signal from the ozone sensing device 400 indicating that the ozone level is below the threshold level. At that time, the user may open the lid for retrieving the article(s) from the compartment 122. It should be appreciated that in an alternative exemplary embodiment, the controller 130 can set a maximum operation time and operates the lock 140 to unlock when the maximum operation time expires. As such, the controller can open the lid 120 if the ozone sensing device 400 fails or is defective.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims or the equivalents thereof.

What is claimed is:

1. An apparatus for disinfecting and/or deodorizing an article comprising:
   a cabinet defining a compartment configured to receive the article;
   a regenerative dryer positioned with respect to the compartment and configured to dehydrate air flowing into an ozone generator, the dryer including:
      a housing having an air inlet and an air outlet located downstream from the air inlet, the housing defining a chamber, and
      a dehydrating agent disposed within the chamber for absorbing moisture laden in the air, the dehydrating agent being operatively regenerated by heat for vaporizing and removing moisture in the dehydrating agent when saturated with the moisture,
      an exhaust port for releasing the moisture captured by the dehydrating agent, and
      a valve mechanism operatively connected to the housing, the valve mechanism including a piston and a solenoid for displacing the piston between a first position and a second position,
      wherein in the first position, the piston is spaced from the air outlet to allow dehydrated air to flow from the dryer to the ozone generator, the piston closing the exhaust port,
      wherein in the second position, the piston is spaced from the exhaust port to allow for exhausting of vaporized moisture from the dehydrating agent, the piston closing the air outlet, and
      wherein the solenoid is a coil which is wound at least partially around the piston, wherein energization of the coil moves the piston from the first position to the second position, wherein the heat generated from energization of coil increases temperature of the dehydrating agent releasing the moisture captured therein through the exhaust port;
   the ozone generator in communication with the dryer and positioned with respect to the compartment, the ozone generator being configured to selectively generate ozone, the generated ozone being introduced into the compartment;
   an ozone conversion device positioned with respect to the compartment and configured to selectively convert ozone back to oxygen; and
   a controller configured to selectively activate the dryer, ozone generator and ozone conversion device.

2. The apparatus of claim 1, wherein the controller is configured to regenerate the dehydrating agent of the dryer after a predetermined number of cycles of ozone generation.

3. The apparatus of claim 1, further including a heater for regenerating the dehydrating agent.

4. The apparatus of claim 1, further including a bias mechanism for urging the piston towards the first position, the bias mechanism being compressed by the piston in the second position.

5. The apparatus of claim 1, wherein the ozone conversion device includes a fan and at least one of a heater and a catalyst, wherein in a first airflow mode, the heater is de-energized and the fan circulates generated ozone through the compartment, the ozone airflow bypassing the catalyst, wherein in a second airflow mode, the heater is energized and the fan directs the heated ozone airflow to the catalyst for converting ozone back to oxygen.

6. The apparatus of claim 5, wherein the fan directs heat generated from the heater into the compartment to remove any residual ozone odor left in the article.

7. The apparatus of claim 1, further comprising a sensing device positioned with respect to the compartment, the sensing device configured to detect a level of the ozone within the compartment and generate a signal representative of the level of ozone, wherein the controller is in signal communication with the sensing device and is configured to operate the ozone generator in response to the signal transmitted from the sensing device.

8. The apparatus of claim 7, wherein the controller is configured to cycle the ozone generator between a first predetermined ozone concentration value and a second predetermined ozone concentration value, wherein the sensing device is configured to monitor the rate of decline of the ozone level within the compartment from the first ozone concentration value to the second ozone concentration value, wherein the controller is configured to compare the sensed rate of decline to a predetermined rate of decline, wherein the controller is configured to continue the cycling of the ozone generator at least until the sensed rate of decline is approximately equal to the predetermined rate of decline.

9. The apparatus of claim 8, wherein the controller is configured to compare the sensed rate of decline between successive cycles to determine a level of odor and/or bacteria remaining in the article.

10. An apparatus for disinfecting and/or deodorizing an article comprising:
    a cabinet defining a compartment configured to receive the article;
    a regenerative dryer positioned with respect to the compartment and configured to dehydrate air flowing into the compartment;
    an ozone generator in communication with the dryer and positioned with respect to the compartment, the ozone generator being configured to selectively generate ozone, the generated ozone being introduced into the compartment;
    an ozone conversion device positioned with respect to the compartment and configured to selectively convert ozone to oxygen, the ozone conversion device including a fan and a housing for housing at least one of a heater and a catalyst, wherein in a first airflow mode, the heater is de-energized and the fan circulates generated ozone through the compartment, the ozone airflow bypassing the catalyst, wherein in a second airflow mode, the heater is energized and the fan directs the heated ozone airflow to the catalyst for converting ozone back to oxygen to be at least partially circulated directly into the compartment;

a controller configured to selectively activate the dryer, ozone generator and ozone conversion device; and wherein the regenerative dryer further includes an exhaust port for releasing moisture captured by a dehydrating agent, and further comprising a valve mechanism including a piston and solenoid for displacing the piston between a first position and a second position, wherein the solenoid is a coil which is wound at least partially around the piston, wherein energization of the coil moves the piston from the first position to the second position, wherein the heat generated from energization of the coil increases temperature of the dehydrating agent releasing the moisture captured therein through the exhaust port, wherein in the first position, the piston is spaced from the air outlet to allow dehydrated air to flow from the dryer to the ozone generator, the piston closing the exhaust port, wherein in the second position, the piston is spaced from the exhaust port to allow for exhausting of vaporized moisture from the dehydrating agent, the piston closing the air outlet.

11. The apparatus of claim 10, wherein the dryer includes a desiccant for reducing a relative humidity of air flowing through the dryer, and a heater for vaporizing and removing moisture in the desiccant when saturated with the moisture.

12. The apparatus of claim 10, wherein the ozone conversion device further includes a damper for redirecting the ozone through the heater and/or catalyst.

13. The apparatus of claim 10, wherein the fan directs heat generated from the heater into the compartment to remove any residual ozone odor left in the article.

14. An apparatus for disinfecting and/or deodorizing an article comprising:

a cabinet defining a compartment configured to receive the article;

a regenerative dryer positioned with respect to the compartment and configured to dehydrate air flowing into the compartment;

an ozone generator in communication with the dryer and positioned with respect to the compartment, the ozone generator being configured to selectively generate ozone, the generated ozone being introduced into the compartment;

an ozone conversion device positioned with respect to the compartment and configured to selectively convert ozone to oxygen, the ozone conversion device including a reversible fan and a housing for housing at least one of a heater and a catalyst, the ozone conversion device further includes a first check valve and a second check valve, wherein in the first air mode, the heater is de-energized and the fan circulates generated ozone through the compartment, the ozone airflow bypassing the catalyst, the first check valve is in an open condition and the second check valve is in a closed condition and the fan directs the ozone in a first direction, wherein in the second air mode, the heater is energized and the fan directs the heated ozone airflow to the catalyst for converting ozone back to oxygen, the first check valve is in a closed condition and the second check valve is in an open condition and the fan directs the ozone in a second, reverse direction; and a controller configured to selectively activate the dryer, ozone generator and ozone conversion device.

15. The apparatus of claim 14, wherein the fan directs heat generated from the heater into the compartment to remove any residual ozone odor left in the article.

16. The apparatus of claim 14, further comprising a sensing device positioned with respect to the compartment, the sensing device configured to detect a level of the ozone within the compartment and generate a signal representative of the level of ozone, wherein the controller is in signal communication with the sensing device and is configured to operate the ozone generator in response to the signal transmitted from the sensing device.

17. The apparatus of claim 16, wherein the controller is configured to compare the sensed rate of decline between successive cycles to determine a level of odor and/or bacteria remaining in the article.

18. The apparatus of claim 16, wherein the controller is configured to cycle the ozone generator between a first predetermined ozone concentration value and a second predetermined ozone concentration value, wherein the sensing device is configured to monitor the rate of decline of the ozone level within the compartment from the first ozone concentration value to the second ozone concentration value, wherein the controller is configured to compare the sensed rate of decline to a predetermined rate of decline, wherein the controller is configured to continue the cycling of the ozone generator at least until the sensed rate of decline is approximately equal to the predetermined rate of decline.

* * * * *